US009228203B2

(12) United States Patent
Delagrave et al.

(10) Patent No.: US 9,228,203 B2
(45) Date of Patent: Jan. 5, 2016

(54) RECOMBINANT BICISTRONIC FLAVIVIRUS VECTORS

(71) Applicant: Sanofi Pasteur Biologics, LLC, Cambridge, MA (US)

(72) Inventors: Simon Delagrave, Stoneham, MA (US); Nathan Brown, Cambridge, MA (US); Harold Kleanthous, Westford, MA (US); Farshad Guirakhoo, Melrose, MA (US); Alexander A. Rumyantsev, Somerville, MA (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 74 days.

(21) Appl. No.: 13/942,064

(22) Filed: Jul. 15, 2013

(65) Prior Publication Data

US 2013/0295134 A1 Nov. 7, 2013

Related U.S. Application Data

(62) Division of application No. 12/525,209, filed as application No. PCT/US2008/001330 on Jan. 31, 2008, now Pat. No. 8,486,417.

(60) Provisional application No. 60/898,652, filed on Jan. 31, 2007.

(51) Int. Cl.

| | |
|---|---|
| ***A61K 39/12*** | (2006.01) |
| ***A61K 39/145*** | (2006.01) |
| ***C12N 15/86*** | (2006.01) |
| ***C12N 7/00*** | (2006.01) |
| *A61K 39/00* | (2006.01) |

(52) U.S. Cl.

CPC ............ *C12N 15/86* (2013.01); *A61K 39/0011* (2013.01); *A61K 39/12* (2013.01); *A61K 39/145* (2013.01); *C12N 7/00* (2013.01); *A61K 2039/5254* (2013.01); *A61K 2039/5256* (2013.01); *C12N 2760/16134* (2013.01); *C12N 2770/24143* (2013.01); *C12N 2840/203* (2013.01)

(58) Field of Classification Search

None

See application file for complete search history.

(56) References Cited

U.S. PATENT DOCUMENTS

| | | | | |
|---|---|---|---|---|
| 6,497,884 | B1 | 12/2002 | Pletnev et al. | |
| 6,685,948 | B1 * | 2/2004 | Zeng et al. | 424/218.1 |
| 6,893,866 | B1 | 5/2005 | Westaway et al. | |
| 2004/0241821 | A1 | 12/2004 | Andino-Pavlovsky et al. | |

FOREIGN PATENT DOCUMENTS

| | | |
|---|---|---|
| WO | WO-98/37911 A1 | 9/1998 |

OTHER PUBLICATIONS

Fiers et al., "A "universal" human influenza A vaccine," Virus Res. 103(1-2):173-6 (2004).

Fiers et al., "M2e-based universal influenza A vaccine," Vaccine. 27(45):6280-3 (2009).

Guirakhoo et al., "Safety and efficacy of chimeric yellow Fever-dengue virus tetravalent vaccine formulations in nonhuman primates," J Virol. 78(9):4761-75 (2004).

Kuno et al., "Maintaining mosquito cell lines at high temperatures: effects on the replication of flaviviruses," In Vitro Cell Dev Biol. 25(2):193-6 (1989).

Extended European Search Report from European Patent Application No. 08725046.0, dated Jan. 17, 2011.

International Preliminary Report on Patentability from International Application No. PCT/US2008/001330, dated Aug. 13, 2009.

International Search Report from International Application No. PCT/US2008/001330, mailed May 28, 2008.

* cited by examiner

*Primary Examiner* — Stacy B Chen

(74) *Attorney, Agent, or Firm* — Clark & Elbing LLP; Susan M. Michaud

(57) ABSTRACT

This invention relates to bicistronic flavivirus vectors, methods of using such vectors in the prevention and treatment of disease, and methods of making such vectors.

12 Claims, 3 Drawing Sheets

Fig. 1A

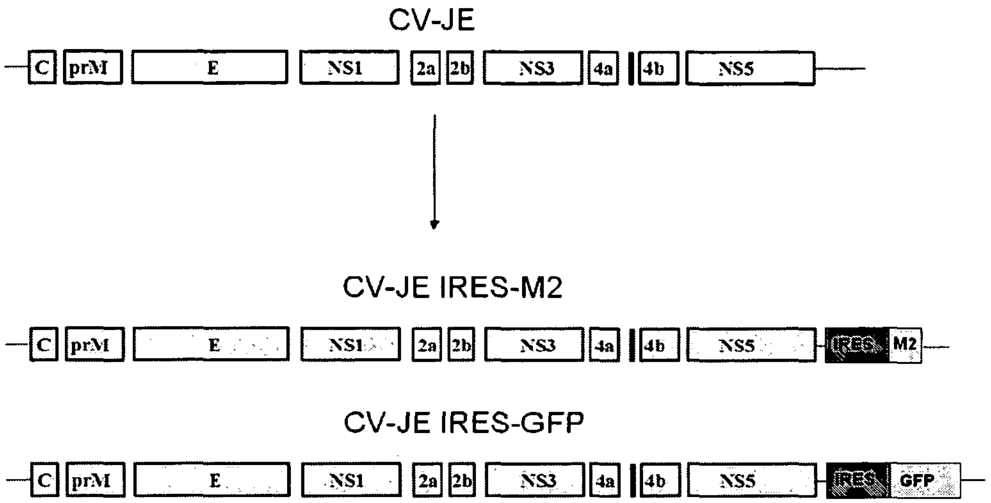

Fig. 1B

GAGAAATACACTGACTACCTAACAGTCATGGACAGGTATTCTGTGGATGCTGACCTGCAACT
GGGTGAGCTTATCTGA[1]AACACCATCTAACAGGAATAACCGGGATACAAACCACGGGTGGAG
AACCGGACTCCCCACAACCTGAAACCGGGATATAAACCACGGCTGGAGAACCGGGCTCCG
CACTTAAAATGAAACAGAAACCGGGATAAAAA[2]CTACGGATGGAGAACCGGACTCCACACAT
TGAGACAGAAGAAGTTGTCAGCCCAGAACCCCACACGAGTTTTGCCACTGCTAAGCTGTGA
GGCAGTGCAGGCTGGGACAGCCGACCTCCAG

[1] TGA stop codon at the end of the viral genome
[2] The end of the deletion

Fig. 1

IRES M2 $10^{-1}$ | IRES M2 $10^{-3}$ | IRES M2 $10^{-3}$

37°C P1, infect Vero at 37°C, detect after 5 days with anti-M2

34°C P1, infect Vero at 34°C, detect after 6 days with anti-M2

34°C P1, infect Vero at 37°C, detect after 6 days with anti-M2

RECOMBINANT BICISTRONIC FLAVIVIRUS VECTORS

CROSS-REFERENCE TO RELATED APPLICATIONS

This application is a divisional application of U.S. patent application Ser. No. 12/525,209, filed Oct. 23, 2009 (now U.S. Pat. No. 8,486,417), which claims priority under 35 U.S.C. §371 from International Application No. PCT/US2008/001330, filed Jan. 31, 2008, which claims benefit of U.S. Provisional Patent Application No. 60/898,652, filed Jan. 31, 2007.

FIELD OF THE INVENTION

This invention relates to recombinant bicistronic flavivirus vectors, methods of using such vectors in the prevention and treatment of disease, and methods of making such vectors.

BACKGROUND OF THE INVENTION

Vaccination is one of the greatest achievements of medicine, and has spared millions of people the effects of devastating diseases. Before vaccines became widely used, infectious diseases killed thousands of children and adults each year in the United States alone, and so many more worldwide. Vaccination is widely used to prevent and treat infection by bacteria, viruses, and other pathogens, and also is an approach that is used in the prevention and treatment of cancer. Several different approaches are used in vaccination, including the administration of killed pathogen, live-attenuated pathogen, and inactive pathogen subunits. In the case of viral infection, live vaccines have been found to confer the most potent and durable protective immune responses.

Live-attenuated vaccines have been developed against flaviviruses, which are small, enveloped, positive-strand RNA viruses that are generally transmitted by infected mosquitoes and ticks. The *Flavivirus* genus of the Flaviviridae family includes approximately 70 viruses, many of which, such as yellow fever (YF), dengue (DEN), Japanese encephalitis (JE), and tick-borne encephalitis (TBE) viruses, are major human pathogens (rev. in Burke and Monath, Fields Virology, $4^{th}$ Ed., p. 1043-1126, 2001).

Different approaches have been used in the development of vaccines against flaviviruses. In the case of yellow fever virus, for example, two vaccines (yellow fever 17D and the French neurotropic vaccine) were developed by serial passage (Monath, "Yellow Fever," In Plotkin and Orenstein, Vaccines, $3^{rd}$ ed., Saunders, Philadelphia, pp. 815-879, 1999). Another approach to attenuation of flaviviruses for use in vaccination involves the construction of chimeric flaviviruses, which include components of two (or more) different flaviviruses. Understanding how such chimeras are constructed requires an explanation of flavivirus structure.

*Flavivirus* proteins are produced by translation of a single, long open reading frame to generate a polyprotein, which is followed by a complex series of post-translational proteolytic cleavages of the polyprotein by a combination of host and viral proteases to generate mature viral proteins (Amberg et al., J. Virol. 73:8083-8094, 1999; Rice, "Flaviviridae," In *Virology*, Fields (ed.), Raven-Lippincott, New York, 1995, Volume I, p. 937). The virus structural proteins are arranged in the polyprotein in the order C-prM-E, where "C" is capsid, "prM" is a precursor of the viral envelope-bound M protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polyprotein.

Chimeric flaviviruses have been made that include structural and non-structural proteins from different flaviviruses. For example, the so-called ChimeriVax™ technology employs the yellow fever 17D virus capsid and nonstructural proteins to deliver the envelope proteins (M and E) of other flaviviruses (see, e.g., Chambers et al., J. Virol. 73:3095-3101, 1999). This technology has been used to develop vaccine candidates against dengue, Japanese encephalitis (JE), West Nile (WN), and St. Louis encephalitis (SLE) viruses (see, e.g., Pugachev et al., in New Generation Vaccines, $3^{rd}$ ed., Levine et al., eds., Marcel Dekker, New York, Basel, pp. 559-571, 2004; Chambers et al., J. Virol. 73:3095-3101, 1999; Guirakhoo et al., Virology 257:363-372, 1999; Monath et al., Vaccine 17:1869-1882, 1999; Guirakhoo et al., J. Virol. 74:5477-5485, 2000; Arroyo et al., Trends Mol. Med. 7:350-354, 2001; Guirakhoo et al., J. Virol. 78:4761-4775, 2004; Guirakhoo et al., J. Virol. 78:9998-10008, 2004; Monath et al., J. Infect. Dis. 188:1213-1230, 2003; Arroyo et al., J. Virol. 78:12497-12507, 2004; and Pugachev et al., Am. J. Trop. Med. Hyg. 71:639-645, 2004).

ChimeriVax™-based vaccines have been shown to have favorable properties with respect to properties such as replication in substrate cells, low neurovirulence in murine models, high attenuation in monkey models, high genetic and phenotypic stability in vitro and in vivo, inefficient replication in mosquitoes (which is important to prevent uncontrolled spread in nature), and the induction of robust protective immunity in mice, monkeys, and humans following administration of a single dose, without serious post-immunization side effects. Indeed, the ChimeriVax™-JE vaccine virus, containing the prM-E genes from the SA14-14-2 JE virus (live attenuated JE vaccine used in China), was successfully tested in preclinical and Phase I and II clinical trials (Monath et al., Vaccine 20:1004-1018, 2002; Monath et al., J. Infect. Dis. 188:1213-1230, 2003). Similarly, successful Phase I clinical trials have been conducted with a ChimeriVax™-WN vaccine candidate, which contains prM-E sequences from a West Nile virus (NY99 strain), with three specific amino acid changes incorporated into the E protein to increase attenuation (Arroyo et al., J. Virol. 78:12497-12507, 2004).

In addition to being used as vaccines against flavivirus infection, flaviviruses, such as chimeric flaviviruses, have been proposed for use as vectors for the delivery of other, non-flavivirus peptides. In one example of such a use, a rational approach for insertion of foreign peptides into the envelope protein of YF 17D virus was described, based on knowledge of the tertiary structure of the flavivirus particle, as resolved by cryoelectron microscopy and fitting the known X-ray structure of the protein dimer into an electron density map (Rey et al., Nature 375:291-298, 1995; Kuhn et al., Cell 108:717-725, 2002). The three-dimensional structure of the protein trimer in its post-fusion conformation has also been resolved (Modis et al., Nature 427:313-319, 2004; Bressanelli et al., EMBO J. 23:728-738, 2004). Galler and co-workers examined the three-dimensional structures of the envelope protein dimer and trimer and concluded that the fg loop of dimerization domain II should be solvent-exposed in both the dimer and trimer conformations. They used this loop to insert malaria humoral and T-cell epitopes into the envelope protein of YF 17D virus and recovered a few viable mutants (Bonaldo et al., J. Virol. 79:8602-8613, 2005; Bonaldo et al., J. Mol. Biol. 315:873-885, 2002; WO 02/072835). Use of this approach, however, does not ensure that a selected site is permissive/optimal for the insertion of every desired foreign peptide in terms of efficient virus replication (as evidenced by some of the Galler et al. data), immunogenicity, and stability. Further, this approach is not applicable to viral proteins for which three-dimensional structures are unknown (e.g., prM/M, NS1, and most other NS proteins of flaviviruses).

In another approach, the envelope protein of ChimeriVax™-JE was probed for permissive insertion sites using a transposon. According to this approach, an inserted transposon in a viable mutant virus is replaced with a desired foreign peptide (see, e.g., WO 02/102828). In yet another approach, foreign sequences were inserted into the yellow fever virus strain YF-17D, downstream of the polyprotein open reading frame (US 2004/0241821).

SUMMARY OF THE INVENTION

The invention provides chimeric flaviviruses that include structural proteins (e.g., membrane/pre-membrane and envelope proteins) of a first flavivirus and non-structural proteins of a yellow fever virus, wherein the genome of the chimeric flavivirus includes an internal ribosome entry site (IRES) and a transgene. The first flavivirus can be, for example, selected from the group consisting of Japanese encephalitis, Dengue-1, Dengue-2, Dengue-3, Dengue-4, Murray Valley encephalitis, St. Louis encephalitis, West Nile, Kunjin, Rocio encephalitis, Ilheus, Tick-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses. Further, the IRES can be located in the 3'-untranslated region of the flavivirus (see, e.g., below).

The transgene of the chimeric flaviviruses of the invention can encode, for example, a vaccine antigen, which can be derived from, e.g., an infectious agent, such as an influenza virus. Exemplary influenza antigens that can be encoded by transgenes, according to the invention, include hemagglutinin, neuraminidase, and M2, and immunogenic fragments thereof (e.g., a fragment including or a fragment of the M2e region of M2). In other examples, the vaccine antigen is a tumor-associated antigen.

The invention also includes flaviviruses (e.g., a yellow fever virus or a chimeric flavivirus, such as a chimeric flavivirus as described above and elsewhere herein) that include an internal ribosome entry site and a transgene encoding an influenza antigen or an immunogenic fragment thereof. In one example, the influenza antigen is an M2 antigen or an immunogenic fragment thereof (e.g., a fragment including or a fragment of the M2e region of the M2 protein).

Further, the invention includes methods of administering to subjects proteins or peptides to subjects, which methods include administering the flaviviruses (e.g., chimeric flaviviruses) described above and elsewhere herein. The administered proteins or peptides can be used in the induction of a prophylactic or therapeutic immune response against the source of the protein or peptide. Thus, the methods of the invention can be vaccination methods and certain compositions of the invention are vaccines.

In addition, the invention includes nucleic acid molecules encoding the flaviviruses (e.g., chimeric flaviviruses) described above and elsewhere herein, as well as pharmaceutical compositions including such flaviviruses. The pharmaceutical compositions are, in general, suitable for administration to humans and, optionally, may include pharmaceutically acceptable carriers and/or diluents. The compositions may also be in lyophilized form. Further, the compositions may be vaccine compositions.

The invention also includes methods of producing flaviviruses (e.g., chimeric flaviviruses) as described above and elsewhere herein. In these methods, cells into which RNA corresponding to the virus has been introduced are cultured at a temperature below 37° C. (e.g., at 31° C.-36° C. or at 34° C.).

Further, the invention includes methods of propagating flaviviruses (e.g., chimeric flaviviruses) as described above and elsewhere herein. In these methods, cells infected with the flaviviruses are incubated at a temperature below 37° C. (e.g., at 31° C.-36° C. or at 34° C.).

The invention provides several advantages. For example, the live, attenuated, viral vectors of the invention induce strong, long-lasting immune responses against specific antigens. The vectors of the invention can be used to confer immunity to infectious diseases, such as influenza, or to disease-related proteins such as cancer antigens and the like. As an example, the invention can be used to deliver influenza virus M2e, which is the external portion of M2, a minor influenza A surface protein that is conserved among diverse influenza viruses and may serve as the basis for a vaccine that protects against all influenza A strains (Neirynck et al., Nat. Med. 5(10):1157-1163, 1999; Fiers et al., Virus Res. 103(1-2):173-176, 2004).

An additional advantage of the vectors of the invention is that, as described further below, they can be used to deliver relatively large antigens, as compared to many previously known viral vectors. Thus, as an example, in addition to M2e, the vectors of the invention can advantageously be used to administer larger portions of M2 or even full length M2.

The advantages of using live vectors, such as the flavivirus-based vectors of the invention, also include (i) expansion of the antigenic mass following vaccine inoculation; (ii) the lack of need for an adjuvant; (iii) the intense stimulation of innate and adaptive immune responses (YF 17D, for example, is the most powerful known immunogen); (iv) the possibility of more favorable antigen presentation due to, e.g., the ability of ChimeriVax™ (derived from YF 17D) to infect antigen presenting cells, such as dendritic cells and macrophages; (v) the possibility to obtain a single-dose vaccine providing life-long immunity; (vi) the envelopes of ChimeriVax™ vaccine viruses are easily exchangeable, giving a choice of different recombinant vaccines, some of which are more appropriate than the others in different geographic areas or for sequential use; (vii) the possibility of modifying complete live flavivirus vectors into packaged, single-round-replication replicons, in order to eliminate the chance of adverse events or to minimize the effect of anti-vector immunity during sequential use; and (viii) the low cost of manufacture.

Additional advantages provided by the invention relate to the fact that chimeric flavivirus vectors of the invention are sufficiently attenuated so as to be safe, and yet are able to induce protective immunity to the flaviviruses from which the proteins in the chimeras are derived and, in particular, the proteins or peptides inserted into the chimeras. Additional safety comes from the fact that some of the vectors used in the invention are chimeric, thus eliminating the possibility of reversion to wild type. An additional advantage of the vectors of the invention is that flaviviruses replicate in the cytoplasm of cells, so that the virus replication strategy does not involve integration of the viral genome into the host cell, providing an important safety measure. Further, a single vector of the invention can be used to deliver multiple epitopes from a single antigen, or epitopes derived from more than one antigen.

An additional advantage provided by the invention relates to the identification of new growth conditions for propagating viral vectors, such as those described herein. As is discussed further below, these conditions enable the production of relatively high titer virus, with increased immunogenicity.

Other features and advantages of the invention will be apparent from the following detailed description, the drawings, and the claims.

BRIEF DESCRIPTION OF THE DRAWINGS

FIG. 1A is a schematic illustration of the CV-JE IRES-M2 and CV-JE IRES-GFP genomes. A deletion of 136 nucleotides was made in the 3'UTR of the CV-JE genomic cDNA, restriction sites were introduced, and the IRES of EMCV was cloned via these sites along with the M2 gene of influenza A or the $GFP_{S65T}$ gene of *A. victoria*. FIG. 1B provides sequence information concerning the 136 nucleotide deletion (SEQ ID NO:44).

DETAILED DESCRIPTION

Figure 2:
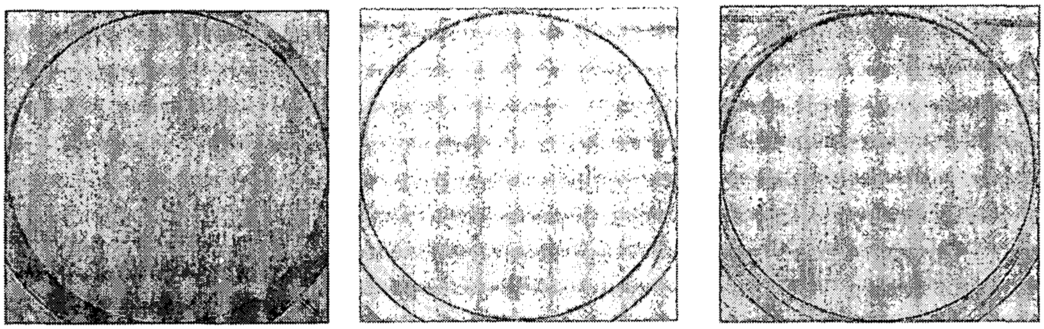
FIG. 2 is an image showing that CV-JE IRES-M2 grows to higher titers and expresses more M2 antigen when propagated at 34° C.

The invention provides viral vectors that can be used in the administration of medically important proteins and peptides, including vaccine antigens. Also included in the invention are methods of using these vectors in methods for preventing and treating diseases or conditions including infectious disease and cancer, pharmaceutical compositions including the vectors, and nucleic acid molecules corresponding to genomes of the viral vectors or the complements thereof. Further, the invention provides methods of making and propagating viral vectors such as those of the invention. The vectors, methods, and compositions of the invention are described further, as follows.

Viral Vectors

In certain examples, the vectors of the invention are based on ChimeriVax™ viruses, which, as described above, consist of a first flavivirus (i.e., a backbone flavivirus) in which a structural protein (or proteins) has been replaced with a corresponding structural protein (or proteins) of a second virus. For example, the chimeras can consist of a first flavivirus in which the prM and E proteins have been replaced with the prM and E proteins of a second flavivirus. As is discussed above, flavivirus proteins, including those of the chimeric flaviviruses described herein, are produced as a polyprotein that is post-translationally cleaved into subunit proteins: the amino terminal structural proteins, capsid (C), pre-membrane (prM), and envelope (E), and the carboxyl terminal non-structural proteins, NS1, NS2A, NS2B, NS3, NS4A, NS4B, and NS5.

The vectors of the invention are flaviviruses (e.g., chimeric flavivirues, as described above) that include one or more internal ribosome entry sites (IRESs), which are nucleotide sequences that allow for translation initiation in the middle of an mRNA sequence, rather than the 5' end, at which translation otherwise normally begins. The IRES is positioned upstream from one or more transgenes encoding one or more proteins or peptides, so that it directs expression of the transgene(s). Examples of types of proteins or peptides that can be expressed in this manner, according to the invention, are proteins or peptides that can be used in prophylactic and therapeutic methods (e.g., vaccine antigens), as well as marker or reporter proteins or peptides that may be used, for example, in diagnostic methods or in screening assays (see below). The IRES/transgene(s) can be present in the flavivirus in a region such as, for example, the 3'-untranslated region, downstream from NS5.

Any of a number of known, naturally-occurring IRES sequences can be included in the viruses of the invention including, e.g., the encephalomyocarditis virus (ECMV) IRES (Clontech, Palo Alto, Calif.), as well as IRES sequences noted in US 2004/0241821, such as those derived from bovine viral diarrhea virus (BVDV), hepatitis C virus, mengovirus, GTX, Cyr61 a, Cyr61b, poliovirus, the immunoglobulin heavy-chain-binding protein (BiP), immunoglobulin heavy chain, picornavirus, murine encephalomyocarditis virus, poliovirus, and foot and mouth disease virus (also see, e.g., WO 96/01324, WO 98/49334, WO 00/44896, and U.S. Pat. No. 6,171,821, which are also referenced in US 2004/0241821). In addition, variants of these sequences (e.g., fragments or sequence variants that are, e.g., at least 70, 80, 90, or 95% identical to naturally occurring IRES sequences) can be used, provided that they can serve as a basis for the initiation of translation. As is shown in the examples provided below, the IRES sequence can be followed by a multiple cloning site, which facilitates the insertion of transgenes under control of the IRES.

The details of two chimeric flaviviruses including IRES/transgene sequences, as described herein, are provided below. As is shown in these examples, vectors of the invention can be made by the insertion of a cassette including an IRES and a transgene into a multiple cloning site engineered in the 3'-untranslated region, e.g., after a 136 nucleotide deletion immediately after the polyprotein stop codon.

The invention also includes the vectors described herein, prior to the insertion of transgene sequences. Such vectors can be used in the generation of vectors including transgene sequences, as described herein.

The chimeric viruses that are used in the invention can be made from any combination of flaviviruses. As is noted above, the chimeras can include structural proteins from a first flavivirus (pre-membrane (prM), envelope (E), and/or capsid (C)) and non-structural proteins from a second, different flavivirus (or flavivirus serotype). For example, the chimeras can include pre-membrane and envelope proteins from a first flavivirus and capsid and non-structural proteins from a second flavivirus.

Specific examples of chimeras that can be used in the invention include yellow fever virus capsid and non-structural sequences, and Japanese encephalitis virus pre-membrane and envelope sequences. However, other viruses can be used as well. Examples of particular flaviviruses that can be used in the invention, as first or second viruses, include mosquito-borne flaviviruses, such as Japanese encephalitis, Dengue (serotypes 1-4), yellow fever, Murray Valley encephalitis, St. Louis encephalitis, West Nile, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses; as well as viruses from the Hepacivirus genus (e.g., Hepatitis C virus).

Details of making chimeric viruses that can be used in the invention are provided, for example, in U.S. Pat. Nos. 6,962,708 and 6,696,281; PCT international applications WO 98/37911 and WO 01/39802; and Chambers et al., J. Virol. 73:3095-3101, 1999, the contents of each of which is incorporated by reference herein in its entirety. In addition, these chimeric viruses can include attenuating mutations, such as those described in the following documents, the contents of each of which is incorporated herein by reference: WO 2003/103571; WO 2005/082020; WO 2004/045529; WO 2006/044857; PCT/US2006/015241; U.S. Pat. No. 6,685,948 B1; U.S. Patent Application Publication US 2004/0052818 A1; U.S. Patent Application Publication 2005/0010043 A1; WO 02/074963; WO 02/095075 A1; WO 03/059384 A1; WO 03/092592 A2; as well as the documents cited above.

A specific example of a type of chimeric virus that can be used in the invention is the human yellow fever virus vaccine strain, YF 17D, in which the prM and E proteins have been replaced with prM and E proteins of another flavivirus, such as Japanese encephalitis virus, West Nile virus, St. Louis encephalitis virus, Murray Valley encephalitis virus, a Dengue virus, or any other flavivirus, such as one of those listed above. For example, the following chimeric flaviviruses, which were deposited with the American Type Culture Collection (ATCC) in Manassas, Va., U.S.A. under the terms of the Budapest Treaty and granted a deposit date of Jan. 6, 1998, can be used in the invention: Chimeric Yellow Fever 17D/Japanese Encephalitis SA14-14-2 Virus (YF/JE A1.3; ATCC accession number ATCC VR-2594) and Chimeric Yellow Fever 17D/Dengue Type 2 Virus (YF/DEN-2; ATCC accession number ATCC VR-2593).

Among the advantages of using the ChimeriVax™ vaccines as vectors, a main advantage is that the envelope proteins (which are the main antigenic determinants of immunity against flaviviruses, and in this case, anti-vector immunity) can be easily exchanged allowing for the construction of several different vaccines using the same YF17D backbone that can be applied sequentially to the same individual. In addition, different recombinant ChimeriVax™ insertion vaccines can be determined to be more appropriate for use in specific geographical regions in which different flaviviruses are endemic, as dual vaccines against an endemic flavivirus and another targeted pathogen. For example, ChimeriVax™-JE-influenza vaccine may be more appropriate in Asia, where JE is endemic, to protect from both JE and influenza, YF17D-influenza vaccine may be more appropriate in Africa and South America, where YF is endemic, ChimeriVax™-WN-influenza may be more appropriate for the U.S. and parts of Europe and the Middle East, in which WN virus is endemic, and ChimeriVax™-Dengue-influenza may be more appropriate throughout the tropics where dengue viruses are present.

In addition to chimeric flaviviruses, other flaviviruses, such as non-chimeric flaviviruses, can be used as vectors according to the present invention.

Examples of such viruses that can be used in the invention include live, attenuated vaccines, such as those derived from the YF 17D strain, which was originally obtained by attenuation of the wild-type Asibi strain (Smithburn et al., "Yellow Fever Vaccination," World Health Organization, p. 238, 1956; Freestone, in Plotkin et al. (eds.), Vaccines, 2$^{nd}$ edition, W.B. Saunders, Philadelphia, U.S.A., 1995). An example of a YF17D strain from which viruses that can be used in the invention can be derived is YF17D-204 (YF-VAX®, Sanofi-Pasteur, Swiftwater, Pa., USA; Stamaril®, Sanofi-Pasteur, Marcy-L'Etoile, France; ARILVAX™, Chiron, Speke, Liverpool, UK; FLAVIMUN®, Berna Biotech, Bern, Switzerland; YF17D-204 France (X15067, X15062); YF17D-204, 234 US (Rice et al., Science 229:726-733, 1985)), while other examples of such strains that can be used are the closely related YF17DD strain (GenBank Accession No. U 17066), YF 17D-213 (GenBank Accession No. U17067), and yellow fever virus 17DD strains described by Galler et al., Vaccines 16(9/10):1024-1028, 1998. In addition to these strains, any other yellow fever virus vaccine strains found to be acceptably attenuated in humans, such as human patients, can be used in the invention.

Further, in addition to live viruses, as discussed above, packaged replicons expressing foreign proteins or peptides can be used in the invention. This approach can be used, for example, in cases in which it may be desirable to increase safety or to minimize antivector immunity (neutralizing antibody response against the envelope proteins), in order to use the same vector for making different vaccines that can be applied to the same individual. Technology for the construction of single-round replicons is well established, and the immunogenic potential of replicons has been demonstrated (Jones et al., Virology 331:247-259, 2005; Molenkamp et al., J. Virol. 77:1644-1648, 2003; Westaway et al., Adv. Virus. Res. 59:99-140, 2003). In an example of such a replicon, most of the prM and E envelope protein genes are deleted. Therefore, it can replicate inside cells, but cannot generate virus progeny (hence single-round replication). It can be packaged into viral particles when the prM-E genes are provided in trans. Still, when cells are infected by such packaged replicon (e.g., following vaccination), a single round of replication follows, without further spread to surrounding cell/tissues.

Protective epitopes from different pathogens can be combined in one virus, resulting in triple-, quadruple-, etc., vaccines. Also, a ChimeriVax™ variant containing the envelope from a non-endemic flavivirus can be used to avoid the risk of natural antivector immunity in a population that otherwise could limit the effectiveness of vaccination in a certain geographical area (e.g., ChimeriVax™-JE vector may be used in the U.S. where JE is not present).

Heterologous Proteins and Peptides

The vectors of the invention can be used to deliver or produce any peptide or protein of prophylactic, therapeutic, diagnostic, or experimental interest. For example, the vectors can be used in the induction of an immune response (prophylactic or therapeutic) against any protein-based antigen that is inserted in connection with an IRES, as described above and elsewhere herein. In some cases, it may be desirable to maintain the size of the flavivirus into which an IRES/transgene is introduced, as much as possible, in order to maintain virus genetic stability and viability. This can be achieved, for example, by the deletion of sequences in the 3'-untranslated region of the virus (see below and also U.S. Pat. No. 6,685,948; US 2005/0010043 A1; PCT/US2006/015241; WO 02/074963; WO 02/095075 A1; WO 03/059384 A1; and WO 03/092592 A2; also see Deubel et al., "Biological and Molecular Variations of Yellow Fever Virus Strains," In Saluzzo et al. (eds.), "Factors in the Emergence of Arbovirus Diseases" Elsevier, Paris, 1997, pages 157-165).

In another example, portions of the NS1 gene (e.g., all or most of the NS1 gene) can be deleted to accommodate an insert. The elimination of NS1 (ΔNS1), which is about 1.2 kb in length, allows the insertion of transgenes similar in size. A consequence of this deletion is that the NS1 function must now be supplied in trans by introduction of the NS1 gene into the cell line used to produce a ΔNS1 chimera (see, e.g., Lindenbach et al., J. Virol. 71:9608-9617, 1997). The chimeric viral particles produced in this way can infect cells, but are not capable of replication in vivo. This creates an antigen gene-delivery vector, which, in addition to avoiding potential problems with genome size limitations, has different properties from the replication-competent chimeras described above (e.g., decreased virulence).

Antigens that can be used in the invention can be derived from, for example, infectious agents such as viruses, bacteria, and parasites. A specific example of such an infectious agent is influenza viruses, including those that infect humans (e.g., A (e.g., strain A/HK/8/68), B, and C strains), as well as avian influenza viruses. Examples of antigens from influenza viruses include those derived from hemagglutinin (HA; e.g., any one of H1-H16, or subunits thereof) (or HA subunits HA1 and HA2), neuraminidase (NA; e.g., any one of N1-N9), M2 (e.g., M2e), M1, nucleoprotein (NP), and B proteins. For example, peptides including the hemagglutinin precursor protein cleavage site (HA0) (e.g., NIPSIQSRGLFGAIAGFIE (SEQ ID NO:1) for A/H1 strains, NVPEKQTRGIFGAIAGFIE (SEQ ID NO:2) for A/H3 strains, and PAKLLKERGFFGAIAGFLE (SEQ ID NO:3) for influenza B strains) or M2e (e.g., GGSLLTEVETPIRNEWGSRSNDSSDGGFEP (SEQ ID NO:4); and $(G)_{1-2}$MSLLTEVETPIRGG (SEQ ID NO:5 and 6), which includes an N-terminal one- or two-glycine linker, followed by the first 12 amino acids of influenza protein M2, followed in turn by a C-terminal two-glycine linker; also see European Patent No. 0 996 717 B1, the contents of which are incorporated herein by reference) can be used. Other examples of peptides that are conserved in influenza can be used in the invention and include: NBe peptide conserved for influenza B (e.g., consensus sequence MNNATFNYTNVNPISHIRGS (SEQ ID NO:7)); the extracellular domain of BM2 protein of influenza B (e.g., consensus MLEPFQ (SEQ ID NO:8)); and the M2e peptide from the H5N1 avian flu (e.g., MSLLTEVETLTRNGWGCRCSDSSD (SEQ ID NO:9)). Use of influenza virus M2 (or fragments thereof, such as M2e) is particularly advantageous, because the sequence of this protein is highly conserved, as compared with the sequences of other influenza proteins (see, e.g., European Patent 0 996 717 B1).

Further examples of influenza proteins and peptides that can be used in the invention, as well as proteins from which such peptides can be derived (e.g., by fragmentation) are described in US 2002/0165176, US 2003/0175290, US 2004/0055024, US 2004/0116664, US 2004/0219170, US 2004/0223976, US 2005/0042229, US 2005/0003349, US 2005/0009008, US 2005/0186621, U.S. Pat. No. 4,752,473, U.S. Pat. No. 5,374,717, U.S. Pat. No. 6,169,175, U.S. Pat. No. 6,720,409, U.S. Pat. No. 6,750,325, U.S. Pat. No. 6,872,395, WO 93/15763, WO 94/06468, WO 94/17826, WO 96/10631, WO 99/07839, WO 99/58658, WO 02/14478, WO 2003/102165, WO 2004/053091, WO 2005/055957, and Tables 1-4 (and references cited therein), the contents of which are incorporated by reference.

Protective epitopes from other human/veterinary pathogens, such as parasites (e.g., malaria), other pathogenic viruses (e.g., human papilloma virus (HPV), herpes simplex viruses (HSV), human immunodeficiency viruses (HIV), and hepatitis C viruses (HCV)), and bacteria (e.g., *Mycobacterium tuberculosis, Clostridium difficile*, and *Helicobacter pylori*) can also be included in the vectors of the invention. Examples of additional pathogens, as well as antigens and epitopes from these pathogens, which can be used in the invention are provided in WO 2004/053091, WO 03/102165, WO 02/14478, and US 2003/0185854, the contents of which are incorporated herein by reference. Further, additional therapeutic protein/antigen sources that can be included in the vectors of the present invention are listed in US 2004/0241821, which is incorporated herein by reference.

Additional examples of pathogens from which antigens can be obtained are listed in Table 5, below, and specific examples of such antigens include those listed in Table 6. In addition, specific examples of epitopes that can be inserted into the vectors of the invention are provided in Table 7. As is noted in Table 7, epitopes that are used in the vectors of the invention can be B cell epitopes (i.e., neutralizing epitopes) or T cell epitopes (i.e., T helper and cytotoxic T cell-specific epitopes).

The vectors of the invention can be used to deliver antigens in addition to pathogen-derived antigens. For example, the vectors can be used to deliver tumor-associated antigens for use in immunotherapeutic methods against cancer. Numerous tumor-associated antigens are known in the art and can be administered according to the invention. Examples of cancers (and corresponding tumor associated antigens) are as follows: melanoma (NY-ESO-1 protein (specifically CTL epitope located at amino acid positions 157-165), CAMEL, MART 1, gp100, tyrosine-related proteins TRP1 and 2, and MUC1)); adenocarcinoma (ErbB2 protein); colorectal cancer (17-1A, 791 Tgp72, and carcinoembryonic antigen); prostate cancer (PSA1 and PSA3). Heat shock protein (hsp110) can also be used as such an antigen. (Also see, e.g., US 2004/0241821 for additional examples.)

In another example of the invention, exogenous proteins that encode an epitope(s) of an allergy-inducing antigen to which an immune response is desired can be used.

The size of the protein or peptide that is inserted into the vectors of the invention can range in length from, for example, from 5-1500 amino acids in length, for example, from 10-1000, 15-500, 20-250, 25-100, 30-55, or 35-45 amino acids in length, as can be determined to be appropriate by those of skill in the art. In addition, the proteins or peptides noted herein can include additional sequences or can be reduced in length, also as can be determined to be appropriate by those skilled in the art. Further, as is described elsewhere herein, deletions can be made in the vectors of the invention to accommodate different sized inserts, as determined to be appropriate by those of skill in the art.

Production and Administration

The viruses described above can be made using standard methods in the art. For example, an RNA molecule corresponding to the genome of a virus can be introduced into primary cells, chicken embryos, or diploid cell lines, from which (or from the supernatants of which) progeny virus can then be purified. Other methods that can be used to produce the viruses employ heteroploid cells, such as Vero cells (Yasumura et al., Nihon Rinsho 21:1201-1215, 1963). In an example of such methods, a nucleic acid molecule (e.g., an RNA molecule) corresponding to the genome of a virus is introduced into the heteroploid cells, virus is harvested from the medium in which the cells have been cultured, harvested virus is treated with a nuclease (e.g., an endonuclease that degrades both DNA and RNA, such as Benzonase™; U.S. Pat. No. 5,173,418), the nuclease-treated virus is concentrated (e.g., by use of ultrafiltration using a filter having a molecular weight cut-off of, e.g., 500 kDa), and the concentrated virus is formulated for the purposes of vaccination. Details of this method are provided in WO 03/060088 A2, which is incorporated herein by reference. Further, methods for producing chimeric viruses are described in the documents cited above in reference to the construction of chimeric virus constructs.

The vectors of the invention are administered to subjects (e.g., humans and non-human animals, such as horses, livestock, and domestic pets (e.g., cats and dogs)) in amounts and by using methods that can readily be selected by persons of ordinary skill in this art. In the case of chimeric flaviviruses and yellow fever virus-based vectors, the vectors can be administered and formulated, for example, in the same manner as the yellow fever 17D vaccine, e.g., as a clarified suspension of infected chicken embryo tissue, or a fluid harvested from cell cultures infected with the chimeric yellow fever virus. The vectors of the invention can thus be formulated as sterile aqueous solutions containing between 100 and 1,000,000 infectious units (e.g., plaque-forming units or tissue culture infectious doses) in a dose volume of 0.1 to 1.0 ml, to be administered by, for example, intramuscular, subcutaneous, or intradermal routes (see, e.g., WO 2004/0120964 for details concerning intradermal vaccination approaches). In addition, because flaviviruses may be capable of infecting the human host via the mucosal routes, such as the oral route (Gresikova et al., "Tick-borne Encephalitis," In *The Arboviruses, Ecology and Epidemiology*, Monath (ed.), CRC Press, Boca Raton, Fla., 1988, Volume IV, 177-203), the vectors can be administered by a mucosal route. The vectors of the invention can be administered in "effective amounts," which are amounts sufficient to produce a desired effect, such as induction of an immune response (e.g., a specific immune response) and/or amelioration of one or more symptoms of a disease or condition.

When used in immunization methods, the vectors can be administered as primary prophylactic agents in adults or children (or animals; see above) at risk of infection by a particular pathogen. The vectors can also be used as secondary agents for treating infected subjects by stimulating an immune response against the pathogen from which the peptide antigen is derived. Further, an epitope, peptide, or protein is "administered" to a subject according to the methods described herein, whether it is present in the material that is actually administered, or is generated by progeny viruses that replicate from the administered material.

For vaccine applications, optionally, adjuvants that are known to those skilled in the art can be used. Adjuvants that can be used to enhance the immunogenicity of the chimeric vectors include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In the case of a chimeric vector delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the vectors. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses. In addition to vaccine applications, as those skilled in the art can readily understand, the vectors of the invention can be used in gene therapy methods to introduce therapeutic gene products into a patient's cells and in cancer therapy.

The invention also provides methods for producing the viral vectors described herein, in which cells (e.g., Vero cells) transfected with RNA corresponding to the vectors are advantageously cultured at a temperature below 37° C., e.g., 30-37° C., 31-36° C., 32-35° C., or 33-34° C. As is described further below, culturing of such transfected cells at 34° C. resulted in the production of virus at higher titers, and with increased antigen production. Thus, the invention provides an improved method for the production of flavivirus vaccines, such as those described herein.

In one example of a viral vector production method of the invention, $1.5\times10^7$ Vero cells received as a suspension are electroporated with an undetermined amount of RNA at 320 Volts, 950 μF in a 0.4 cm gap cuvette (the concentration of RNA is unknown, because the amount of synthesized RNA is very small). After electroporation, the cells are added to a 75 $cm^2$ flask and incubated at 34° C., 5% $CO_2$ for seven days. CPE typically is not observed in the electroporated cells. The cell culture media is MEM supplemented with 5% heat-inactivated FBS, 2 mM L-Glutamine, and 0.2% Sodium Bicarbonate.

In addition to the above-described uses, the vectors of the invention can also be used in methods for identifying antiviral drugs by using the IRES to drive translation of a reporter gene such as GFP. Such a virus, grown in the presence of an effective antiviral drug, would produce decreased amounts of reporter protein, which could be assayed in a high-throughput fashion.

Experimental Results

ChimeriVax™ technology can be used to induce immunity against antigens that are not of flavivirus origin. For example, to create a universal influenza A vaccine, a gene encoding the M2 protein of influenza A (strain A/HK/8/68) was inserted downstream of an internal ribosome entry site (IRES) derived from encephalomyocarditis virus (EMCV), and the resulting IRES-M2 cassette was inserted into a multiple cloning site, which was engineered in a truncated 3' UTR (136 nucleotide deletion immediately after the polyprotein stop codon) of CV-JE (FIGS. 1A and 1B). A similar bicistronic construct was also prepared by replacing the M2 gene with the eGFP gene.

Details of generating chimeric flaviviruses are provided elsewhere (see e.g., U.S. Pat. Nos. 6,962,708 and 6,696,281; PCT international applications WO 98/37911 and WO 01/39802; and Chambers et al., J. Virol. 73:3095-3101, 1999). This technology was adapted for use in making the vectors of the present invention, as follows.

We created a YF.JE 5'3' vector including a multiple cloning site (MCS) containing Afl II and Sph I restriction sites, while removing a 136 basepair section of vector. To do this, we made two fragments of DNA that overlap with each other to create the MCS. This was achieved by carrying out PCR with two reactions: one with primer MCS 5'3'–(5'-GCATGCCACACACCACTTAAGTCAGATAAGCTCACCCAGTTG-3' (SEQ ID NO:10)) and primer YF 9.595+ (5'-GCACGGATGTGACAGACTGAAG-3' (SEQ ID NO:11)), and the other reaction with primer MCS 5'3'+(5'-CTTAAGTGGTGTGTGGCATGCCTACGGATGGAGAACCGGA-3' (SEQ ID NO:12)) and primer YF 10.84– (5'-AGTGGTTTTGTGTTTGTCATCCAAAGGTC-3' (SEQ ID NO:13)). The template for both reactions was YF.JE 5'3', and PCR was carried out as follows: denature at 94° C. (one minute); 20 cycles of: 94° C. (20 seconds), 50° C. (20 seconds), and 68° C. (1 minute); and 4° C. (hold).

Once these two fragments (YF 9.595+/MCS 5'3'– and YF 10.84–/MCS 5'3'+) were amplified, another PCR reaction was carried out to generate a single fragment, based on their overlap. The complementary tails bind each other, resulting in the joining of the fragments using primers YF 9.595+ and YF 10.84–. The resulting fragment includes Alf II and Sph I restriction sites. To generate this fragment, a PCR reaction containing YF 9.595+/MCS 5'3'– and YF 10.84–/MCS 5'3'+ PCR fragments as template was incubated with no primer at 94° C. (one minute), 94° C. (20 seconds), 50° C. (20 seconds), and 68° C. (1 minute), then primers YF 9.595+ and YF 10.84– were added and the reaction was incubated for 15 cycles of 94° C. (20 seconds), 50° C. (20 seconds), and 68° C. (1 minute); and then held at 4° C. Once the single fragment generated from the overlapping fragments was generated, it was inserted into YF.JE 5'3' by digestion and ligation using Sac and Xba I enzymes, to yield a YF.JE 5'3' plasmid with a MCS containing Afl II and Sph I restriction sites.

An IRES/M2 fragment with Afl II and Sph I restriction sites on its 5' and 3' ends, respectively, was generated to insert into the MCS in YF.JE 5'3', as described above. The first PCR has two reactions: one reaction uses primer IRES Afl II+ (5'-GGTTGGGGTCTTAAGTGCATCTAGGGCGGCCAAT-3' (SEQ ID NO:14)) and primer IRES M2–(5'-ACCTCGGTTAGAAGGCTCATATTATCATCGTGTTTTTCAAAGG-3' (SEQ ID NO:15)), with IRES as the template, and the second reaction uses primer M2+ (5'-ATGAGCCTTCTAACCGAGGT-3' (SEQ ID NO:16)) and primer M2 Sph I-(5'-CCAACCACAGCATGCTTACTCCAGCTCTATGCTGA-3' (SEQ ID NO:17)), with M2 as the template. PCR was carried out as follows: denature at 94° C. (one minute); 15 cycles of: 94° C. (20 seconds), 50° C. (20 seconds), and 68° C. (1 minute); and 4° C. (hold).

The second reaction is an overlap reaction that combines these two fragments together. To generate the combined fragment, a PCR reaction containing IRES Afl 11+1 IRES M2– and M2+/M2 Sph I PCR fragments as template was incubated with no primer at 94° C. (one minute), 94° C. (20 seconds), 50° C. (20 seconds), and 68° C. (1 minute), then primers IRES Afl II+ and M2 Sph I were added and the reaction was incubated for 15 cycles of: 94° C. (20 seconds), 50° C. (20 seconds), and 68° C. (1 minute); and then held at 4° C. The resulting overlapped PCR product is an IRES/M2 fragment that contains Afl II and SphI restrictions sites at its 5' and 3' ends, respectively. Once the fragment is overlapped, it is inserted into YF.JE 5'3'-136 bp MCS by digestion and ligation using Afl II and Sph I enzymes to yield a plasmid containing IRES M2.

The engineered CV-JE genomic cDNA constructs were transcribed into RNA, which was then transfected into Vero cells. Cells incubated at 37° C. produce low titers of the desired virus (~$2\times10^3$ pfu/mL at day 7 post-transfection; Table 8), and expression of M2 appears low, as judged by weak staining of infected cells in an immunofocus assay using anti-M2e antibody (FIG. 2).

Figure 3:
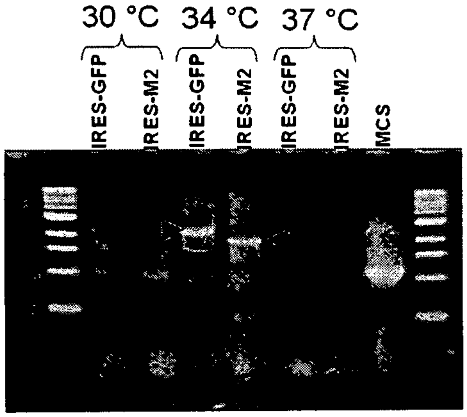
FIG. 3 is an image showing the results of RT-PCR analysis of culture supernatants harvested 7 days post-transfection. RT-PCR was done on RNA extracted from 1 mL of culture supernatant using primers spanning the site of insertion in the 3' UTR. Three genomic RNAs were transfected, CV-JE IRES-M2, CV-JE IRES-GFP, and CV-JE MCS, which comprise the 136 nucleotide deletion and restriction sites for convenient cloning of inserts into the genomic cDNA. Cells were maintained at the indicated temperatures post-transfection for 7 days. MCS-transfected cells were kept at 37° C. Strong bands of the expected sizes (arrow heads) are only visible in 34° C. samples. No-RT controls do not show PCR products.

We investigated the effect on virus yield and antigen expression of maintaining transfected cells at either 30° C., 34° C., or 37° C. Surprisingly, detection of viral RNA in culture supernatant by RT-PCR shows highest amplicon yield when transfected cells are maintained at a temperature of 34° C. (FIG. 3). This was seen for both the IRES-M2 and IRES-GFP viruses.

Similarly, virus titers (Table 8) and antigen expression (FIG. 2 and Table 9) are highest when cells are maintained at 34° C. FIG. 2 shows the results of an immunofocus assay using anti-M2e antibody 14C2 (Affinity BioReagents, Golden, Colo.). CV-JE IRES-M2 RNA was transfected into cells, which were kept in a $CO_2$ incubator for 7 days at 37° C. (37° C. P1), 30° C. (30° C. P1), or 34° C. (34° C. P1). Culture supernatants from each transfection were then diluted ($10^{-1}$ or $10^{-3}$-fold dilution) and added to Vero monolayers in the pictured wells. The infected wells were kept for 5 or 6 days at either 37° C. or 34° C., respectively, then fixed and detected with anti-M2e antibody. The left panel shows approximately 15 M2e-positive plaques, which are difficult to see without image processing. The middle panel shows about $10^2$ plaques, which are clearly visible by eye and in the image. Cells shown in the right panel were infected with the same virus supernatant as the middle panel, but the infected monolayer was kept at 37° C. instead of 34° C. Plaques in this well are not visible by eye or in the image.

Cells infected with the bicistronic GFP-expressing virus also showed improved expression when maintained at 34° C. (Table 9). This is significant, because it shows that the optimal temperature is the same for two different chimeric vaccine constructs.

Thus, we have demonstrated that two bicistronic CV-JE viruses are viable and express different proteins (one of which is a universal influenza A antigen), and shown that these bicistronic chimeras are optimally propagated at 34° C.

TABLE 1

Influenza A virus CTL Epitopes of the Nucleoprotein

| Amino Acid Positions (ref.) | Host | MHC restriction |
|---|---|---|
| 44-52 (ref. 14) | Human | HLA-A1 |
| 50-63 (ref. 3) | Mouse (CBA) | H-2Kk |
| 91-99 (ref. 13) | Human | HLA-Aw68 |
| 147-158 (ref. 5) | Mouse (Balb/c) | H-2Kd |
| 265-273 (ref. 14) | Human | HLA-A3 |
| 335-349 (ref. 1) | Human | HLA-B37 |
| 335-349 (ref. 2) | Mouse | HLA-B37 |
| 365-380 (ref. 2) | Mouse | H-2Db |
| 366-374 (ref. 9) | Mouse (C57B1/6) | H-2Db |
| 380-388 (ref. 16) | Human | HLA-B8 |
| 383-391 (ref. 16) | Human | HLA-B27 |

TABLE 2

Influenza A virus T helper Epitopes of the Nucleoprotein

| Amino Acid Positions (ref.) | Host | MHC restriction |
|---|---|---|
| 55-69 (ref. 8) | Mouse (Balb/c) | H-2Kd |
| 182-205 (ref. 11) | Human | |
| 187-200 (ref. 8) | Mouse (CBA) | H-2Kk |
| | Mouse (Balb/c) | H-2Kd |
| 216-229 (ref. 8) | Mouse (Balb/c) | H-2Kd |
| 206-229 (ref. 11) | Human | HLA-DR1, HLA-DR2 en HLA-DRw13 |
| 260-283 (ref. 8) | Mouse (CBA) | H-2Kk |
| | Mouse (C57B1/6) | H-2Db |
| | Mouse (B10.s) | H-2s |
| 297-318 (ref. 11) | Human | |
| 338-347 (ref. 16) | Human | HLA-B37 |
| 341-362 (ref. 11) | Human | |
| 413-435 (ref. 8) | Mouse (C57B1/6) | H-2Db |

TABLE 3

Influenza A Virus T cell Epitopes of Other Viral Proteins

| Peptide | Host | T cell type | MHC restriction |
|---|---|---|---|
| PB1 (591-599) (ref. 14) | Human | CTL | HLA-A3 |
| HA (204-212) (ref. 16) | Mouse | CTL | H-2Kd |
| HA (210-219) (ref. 16) | Mouse | CTL | H-2Kd |
| HA (259-266) (ref. 16) | Mouse | CTL | H-2Kk |
| HA (252-271) (ref. 7) | Mouse | CTL | H-2Kk |
| HA (354-362) (ref. 16) | Mouse | CTL | H-2Kk |
| HA (518-526) (ref. 16) | Mouse | CTL | H-2Kk |
| HA (523-545) (ref. 10) | Mouse | CTL | |
| NA (76-84) (ref. 16) | Mouse | CTL | H-2Dd |

TABLE 3-continued

Influenza A Virus T cell Epitopes of Other Viral Proteins

| Peptide | Host | T cell type | MHC restriction |
|---|---|---|---|
| NA (192-201) (ref. 16) | Mouse | CTL | H-2Kd |
| M1 (17-29) (ref. 6) | Human | T helper | HLA-DR1 |
| M1 (56-68) (ref. 4) | Human | CTL | HLA-A2 |
| M1 (58-66) (ref. 12) | Human | CTL | HLA-A2 |
| M1 (128-135) (ref. 15) | Human | CTL | HLA-B35 |
| NS1 (122-130) (ref. 15) | Human | CTL | HLA-A2 |
| NS1 (152-160) (ref. 16) | Mouse | CTL | H-2Kk |

REFERENCES (1) McMichael et al., J. Exp. Med. 164:1397-1406, 1986.

(2) Townsend et al., Cell 44:959-968, 1986.

(3) Bastin et al., J. Exp. Med. 165:1508-1523, 1987.

(4) Gotch et al., Nature 326:881-882, 1987.

(5) Bodmer et al., Cell 52:253-258, 1988.

(6) Ceppelini et al., Nature 339:392-394, 1989.

(7) Sweetser et al., Nature 342:180-182, 1989.

(8) Gao et al., J. Immunol. 143:3007-3014, 1989.

(9) Rotzschke et al., Nature 348:252-254, 1990.

(10) Milligan et al., J. Immunol. 145:3188-3193, 1990.

(11) Brett et al., J. Immunol. 147:984-991, 1991.

(12) Bednarek et al., J. Immunol. 147:4047-4053, 1991.

(13) Cerundolo et al., Proc. Roy. Soc. Lond. Series B boil. Sci. 244:169-177, 1991.

(14) DiBrino et al., J. Immunol. 151:5930-5935, 1993.

(15) Dong et al., Eur. J. Immunol. 26:335-339, 1996.

(16) Parker et al., Seminars in Virology 7:61-73, 1996.

TABLE 4

Extracellular Part of M2 Protein of Human Influenza A Strains

| Virus strain (subtype) | |
|---|---|
| A/WS/33 (H1N1) | SLLTEVETPIRNEWGCRCNDSSD[1] |
| A/WSN/33 (H1N1) | SLLTEVETPIRNEWGCRCNDSSD |
| A/NWS/33 (H1N1) | SLLTEVETPIRNEWGCRCNDSSD |
| A/PR/8/34 (H1N1) | SLLTEVETPIRNEWECRCNGSSD[2] |
| A/Fort Monmouth/1/47 (H1N1) | SLLTEVETPTKNEWGCRCNDSSD[3] |
| A/fort Warren/1/50 (H1N1) | SLLTEVETPIRNEWGCRCNDSSD |
| A/JapanxBellamy/57 (H2N1) | SLLTEVETPIRNEWGCRCNDSSD |
| A/Singapore/1/57 (H2N2) | SLLTEVETPIRNEWGCRCNDSSD |
| A/Leningrad/134/57 (H2N2) | SLLTEVETPIRNEWGCRCNDSSD |
| A/Ann Harbor/6/60 (H2N2) | SLLTEVETPIRNEWGCRCNDSSD |
| A/NT/60/68 (hxNy ?) | SLLTEVETPIRNEWGCRCNDSSD |
| A/Aichi/2/68 (H3N2) | SLLTEVETPIRNEWGCRCNDSSD |
| A/Korea/426/68 (H2N2) | SLLTEVETPIRNEWGCRCNDSSD |
| A/Hong Kong/1/68 (H3N2) | SLLTEVETPIRNEWGCRCNDSSD |
| A/Udorn/72 (H3N2) | SLLTEVETPIRNEWGCRCNDSSD |
| A/Port Chalmers/73 (H3N2) | SLLTEVETPIRNEWGCRCNDSSD |
| A/USSR/90/77 (H1N1) | SLLTEVETPIRNEWGCRCNDSSD |
| A/Bangkok/1/79 | SLLTEVETPIRNEWGCRCNDSSD |
| A/Philippines/2/82/BS (H3N2) | SLLTEVETPIRNEWGCRCNGSSD[2] |
| A/NY/83 (H3N2) | SLLTEVETPIRNEWGCRCNDSSD |
| A/Memphis/8/88 (H3N2) | SLLTEVETPIRNEWGCRCNDSSD |
| A/Beijing/353/89 (H3N2) | SLLTEVETPIRNEWGCRCNDSSD |
| A/Guangdong/39/89 (H3N2) | SLLTEVETPIRNEWGCRCNDSSD |
| A/Kitakyushu/159/93 (H3N2) | SLLTEVETPIRNEWGCRCNDSSD |
| A/Hebei/12/93 (H3N2) | SLLTEVETPIRNEWGCRCNDSSD |
| A/Aichi/69/94 (H3N2) | SLLTEVETPIRNEWECRCNGSSD[4] |
| A/Saga/447/94 (H3N2) | SLLTEVETPIRNEWECRCNGSSD[4] |

TABLE 4 -continued

| Extracellular Part of M2 Protein of Human Influenza A Strains | |
|---|---|
| Virus strain (subtype) | |
| A/Sendai/c182/94 (H3N2) | SLLTEVETPIRNEWGCRCNDSSD |
| A/Akita/1/94 (H3N2) | SLLTEVETPIRNEWGCRCNDSSD |
| A/Sendai/c384/94 (H3N2) | SLLTEVETPIRNEWGCRCNDSSD |
| A/Miyagi/29/95 (H3N2) | SLLTEVETPIRNEWGCRCNDSSD |
| A/Charlottesville/31/95 | SLLTEVETPIRNEWGCRCNDSSD |
| A/Akita/1/95 (H3N2) | SLLTEVETPIRNEWECRCNGSSD[4] |
| A/Shiga/20/95 (H3N2) | SLLTEVETPIRNEWGCRCNDSSD |
| A/Tochigi/44/95 (H3N2) | SLLTEVETPIRNEWECRCNGSSD[4] |
| A/Hebei/19/95 (H3N2) | SLLTEVETPIRNEWECRCNGSSD[4] |
| A/Sendai/c373/95 (H3N2) | SLLTEVETPIRNEWECRCNGSSD[4] |
| A/Niigata/124/95 (H3N2) | SLLTEVETPIRNEWECRCNGSSD[4] |
| A/Ibaraki/1/95 (H3N2) | SLLTEVETPIRNEWECRCNGSSD[4] |
| A/Kagoshima/10/95 (H3N2) | SLLTEVETPIRNEWECRCNGSSD[4] |
| A/Gifu/2/95 (H3N2) | SLLTEVETPIRNEWECRCNGSSD[4] |
| A/Osaka/c1/95 (H3N2) | SLLTEVETPIRNEWECRCNGSSD[4] |
| A/Fukushima/140/96 (H3N2) | SLLTEVETPIRNEWGCRCNDSSD |
| A/Fukushima/114/96 (H3N2) | SLLTEVETPIRNEWGCRCNDSSD |
| A/Niigata/137/96 (H3N2) | SLLTEVETPIRNEWGCRCNDSSD |
| A/Hong Kong/498/97 (H3N2) | SLLTEVETPIRNEWGCRCNDSSD |
| A/Hong Kong/497/97 (H3N2) | SLLTEVETPIRNEWGCRCNDSSD |
| A/Hong Kong/470/97 (H1N1) | SLLTEVETPIRNEWGCRCNDSSD |
| A/Shiga/25/97 (H3N2) | SLLTEVETPIRNEWGCRCNDSSD |
| A/Hong Kong/427/98 (H1N1) | SLLTEVETPIRNEWECRCNDSSD[5] |
| A/Hong Kong/1143/99 (H3N2) | SLLTEVETPIRNEWGCRCNDSSD |
| A/Hong Kong/1144/99 (H3N2) | SLLTEVETPIRNEWGCRCNDSSD |
| A/Hong Kong/1180/99 (H3N2) | SLLTEVETPIRNEWGCRCNDSSD |
| A/Hong Kong/1179/99 (H3N2) | SLLTEVETPIRNEWGCRCNDSSD |

[1]All sequences in this table correspond to SEQ ID NO: 45, except if otherwise indicated
[2]SEQ ID NO: 46
[3]SEQ ID NO: 47
[4]SEQ ID NO: 48
[5]SEQ ID NO: 49

TABLE 5

List of examples of pathogens from which epitopes/antigens/peptides can be derived VIRUSES:
Flaviviridae
- Yellow Fever virus
- Japanese Encephalitis virus
- Dengue virus, types 1, 2, 3 & 4
- West Nile Virus
- Tick Borne Encephalitis virus
- Hepatitis C virus (e.g., genotypes 1a, 1b, 2a, 2b, 2c, 3a, 4a, 4b, 4c, and 4d)

TABLE 5-continued

List of examples of pathogens from which epitopes/antigens/peptides can be derived Papoviridae
- Papillomavirus Retroviridae
- Human Immunodeficiency virus, type I
- Human Immunodeficiency virus, type II
- Simian Immunodeficiency virus
- Human T lymphotropic virus, types I & II Hepnaviridae
- Hepatitis B virus TABLE 5-continued

| List of examples of pathogens from which epitopes/antigens/peptides can be derived |
|---|
| Picornaviridae |
| Hepatitis A virus |
| Rhinovirus |
| Poliovirus |
| Herpesviridae |
| Herpes simplex virus, type I |
| Herpes simplex virus, type II |
| Cytomegalovirus |
| Epstein Barr virus |
| Varicella-Zoster virus |
| Togaviridae |
| Alphavirus |
| Rubella virus |
| Paramyxoviridae |
| Respiratory syncytial virus |
| Parainfluenza virus |
| Measles virus |
| Mumps virus |
| Orthomyxoviridae |
| Influenza virus |
| Filoviridae |
| Marburg virus |
| Ebola virus |
| Rotoviridae |
| Rotavirus |
| Coronaviridae |
| Coronavirus |
| Adenoviridae |
| Adenovirus |
| Rhabdoviridae |
| Rabiesvirus |
| BACTERIA: |
| Enterotoxigenic *E. coli* |
| Enteropathogenic *E. coli* |
| *Campylobacter jejuni* |
| *Helicobacter pylori* |
| *Salmonella typhi* |
| *Vibrio cholerae* |
| *Clostridium difficile* |
| *Clostridium tetani* |
| *Streptococccus pyogenes* |
| *Bordetella pertussis* |
| *Neisseria meningitides* |
| *Neisseria gonorrhoea* |
| *Legionella neumophilus* |

TABLE 5-continued

| List of examples of pathogens from which epitopes/antigens/peptides can be derived |
|---|
| *Chlamydial* spp. |
| *Haemophilus* spp. |
| *Shigella* spp. |
| PARASITES: |
| *Plasmodium* spp. |
| *Schistosoma* spp. |
| *Trypanosoma* spp. |
| *Toxoplasma* spp. |
| *Cryptosporidia* spp. |
| *Pneumocystis* spp. |
| *Leishmania* spp. |

TABLE 6

Examples of select antigens from listed viruses

| VIRUS | ANTIGEN |
|---|---|
| Flaviviridae | |
| Yellow Fever virus | Nucleocapsid, M & E glycoproteins |
| Japanese Encephalitis virus | " |
| Dengue virus, types 1, 2, 3 & 4 | " |
| West Nile Virus | " |
| Tick Borne Encephalitis virus | " |
| Hepatitis C virus | Nucleocapsid, E1 & E2 glycoproteins |
| Papoviridae | |
| Papillomavirus | L1 & L2 capsid protein, E6 & E7 transforming protein (oncopgenes) |
| Retroviridae | |
| Human Immunodeficiency virus, type I | gag, pol, vif, tat, vpu, env, nef |
| Human Immunodeficiency virus, type II | " |
| Simian Immunodeficiency virus | " |
| Human T lymphotropic virus, types I & II | gag, pol, env |

TABLE 7

Examples of B and T cell epitopes from listed viruses/antigens

| VIRUS | ANTIGEN | EPITOPE | LOCATION | SEQUENCE (5'-3') |
|---|---|---|---|---|
| | | Flaviviridae | | |
| Hepatitis C | Nucleocapsid | CTL | 2-9 | STNPKPQR (SEQ ID O: 18) |
| | | | 35-44 | YLLPRRGPRL |
| | | | 35-45 | (SEQ ID NO: 19) |
| | | | 41-49 | GPRLGVRAT |
| | | | 41-50 | (SEQ ID NO: 20) |
| | | | 81-100 | YPWPLYGNEGCGWAGWLLSP (SEQ ID NO: 21) |
| | | | 129-144 | GFADLMGYIPLVGAPL (SEQ ID NO: 22) |
| | | | 132-140 | DLMGYIPLV |
| | | | 132-141 | (SEQ ID NO: 23) |
| | | | 178-187 | LLALLSCLTV |
| | | | 178-188 | (SEQ ID NO: 24) |
| | E1 glycoprotein | CTL | 231-250 | REGNASRCWVAVTPTVATRD (SEQ ID NO: 25) |
| | E2 | CTL | 686-694 | STGLIHLHQ (SEQ ID NO: 26) |

TABLE 7 -continued

| Examples of B and T cell epitopes from listed viruses/antigens | | | | |
|---|---|---|---|---|
| VIRUS | ANTIGEN | EPITOPE | LOCATION | SEQUENCE (5'-3') |
| | glycoprotein | | 725-734 | LLADARVCSC (SEQ ID NO: 27) |
| | | | 489-496 | CWHYPPRPCGI (SEQ ID NO: 28) |
| | | | 569-578 | CVIGGVGNNT (SEQ ID NO: 29) |
| | | | 460-469 | RRLTDFAQGW (SEQ ID NO: 30) |
| | | | 621-628 | TINYTIFK (SEQ ID NO: 31) |
| | | B cell | 384-410 | ETHVTGGNAGRTTAGLVGLL TPGAKQN (SEQ ID NO: 32) |
| | | | 411-437 | IQLINTNGSWHINSTALNCNES LNTGW (SEQ ID NO: 33) |
| | | | 441-460 | LFYQHKFNSSGCPERLASCR (SEQ ID NO: 34) |
| | | | 511-546 | PSPVVVGTTDRSGAPTYSWG ANDTDVFVLNNTRPPL (SEQ ID NO: 35) |
| | | T helper | 411-416 | IQLINT (SEQ ID NO: 36) |
| | | Papoviridae | | |
| HPV 16 | E7 | T helper | 48-54 | DRAHYNI (SEQ ID NO: 37) |
| | | CTL | 49-57 | RAHYNIVTF (SEQ ID NO: 38) |
| | | B cell | 10-14 | EYMLD (SEQ ID NO: 39) |
| | | | 38-41 | IDGP (SEQ ID NO: 40) |
| | | | 44-48 | QAEPD (SEQ ID NO: 41) |
| HPV 18 | E7 | T helper | 44-55 | VNHQHLPARRA (SEQ ID NO: 42) |
| | | | 81-90 | DDLRAFQQLF (SEQ ID NO: 43) |

TABLE 8

| P1 virus titers of cultures maintained at different temperatures | | | | | | |
|---|---|---|---|---|---|---|
| P1 temperature | Crystal violet titer (pfu/mL)[a] | | | Immunostaining titer (pfu/mL)[b] | | |
| (° C.) | 30 | 34 | 37 | 30 | 34 | 37 |
| CV-JE IRES-M2 | n.v. | $1 \times 10^6$ | $2 \times 10^3$ | $3 \times 10^4$ | $2 \times 10^6$ | $1.2 \times 10^3$ |
| CV-JE IRES-eGFP | n.v. | $9 \times 10^5$ | $6 \times 10^3$ | n/a | n/a | n/a |

P1 & plaque assay both done at indicated temperature

[a]Crystal violet or neutral red plaque assay

[b]Determined by immunofocus assay n.v. = plaques not visible n/a = not applicable, not done

TABLE 9

| Fluorescence of cells infected with CV-JE IRES-GFP | | | |
|---|---|---|---|
| dilution | 30 C. | 34 C. | 37 C. |
| 1 | 45 | 1284 | 113 |
| 0.1 | 52 | 246 | 67 |
| 0.01 | 41 | −21 | 10 |
| uninfected | 23 | −63 | 40 |

Culture supernatant harvested on day 7 post-transfection was used to infect Vero cells. These were harvested 2 days later, resuspended in PBS and tested for fluorescence using a Wallac Victor2 multilabel counter.

Cells were handled at the indicated temperature throughout the experiment. Undiluted cell suspensions (dilution = 1), 10x, and 100x dilutions (dilution = 0.1 or 0.01) were compared with undiluted, uninfected cells. Background (average fluorescence of uninfected cells) is subtracted from all values in the table.

The contents of all references cited above are incorporated herein by reference. Use of singular forms herein, such as "a" and "the," does not exclude indication of the corresponding plural form, unless the context indicates to the contrary. Thus, for example, if a claim indicates the administration of "a" flavivirus, it can also be interpreted as covering administration of more than one flavivirus, unless otherwise indicated. Other embodiments are within the following claims.

What is claimed is:

1. A method of administering a protein or peptide to a subject, the method comprising administering to the subject a chimeric flavivirus comprising structural sequences of a first flavivirus and non-structural sequences of a yellow fever virus, wherein the genome of said chimeric flavivirus comprises an internal ribosome entry site and a transgene located in the 3'-untranslated region of the flavivirus.

2. The method of claim 1, wherein the chimeric flavivirus comprises pre-membrane and envelope sequences of said first flavivirus, and capsid and non-structural sequences of said yellow fever virus.

3. The method of claim 1, wherein the first flavivirus is selected from the group consisting of Japanese encephalitis, Dengue-1, Dengue-2, Dengue-3, Dengue-4, Murray Valley encephalitis, St. Louis encephalitis, West Nile, Kunjin, Rocio encephalitis, Ilheus, Tick-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

4. The method of claim 1, wherein the first flavivirus is a Japanese encephalitis virus.

5. The method of claim 1, wherein the flavivirus comprises a deletion within the 3'-untranslated region of the flavivirus.

6. The method of claim 1, wherein the transgene encodes a vaccine antigen.

7. The method of claim 6, wherein the vaccine antigen is derived from an infectious agent.

8. The method of claim 7, wherein the infectious agent is an influenza virus.

9. The method of claim 8, wherein the vaccine antigen is selected from the group consisting of hemagglutinin, neuraminidase, or an immunogenic fragment thereof.

10. The method of claim 6, wherein the vaccine antigen is a tumor-associated antigen.

11. A nucleic acid molecule encoding a chimeric flavivirus comprising structural sequences of a first flavivirus and non-structural sequences of a yellow fever virus, wherein the genome of said chimeric flavivirus comprises an internal ribosome entry site and a transgene located in the 3'-untranslated region of the chimeric flavivirus.

12. The nucleic acid molecule of claim 11, wherein the transgene encodes an influenza antigen or an immunogenic fragment thereof.

* * * * *

SEQUENCE LISTING

<160> NUMBER OF SEQ ID NOS: 49

<210> SEQ ID NO 1
<211> LENGTH: 19
<212> TYPE: PRT
<213> ORGANISM: Influenza virus

<400> SEQUENCE: 1

Asn Ile Pro Ser Ile Gln Ser Arg Gly Leu Phe Gly Ala Ile Ala Gly
1 5 10 15

-continued

Phe Ile Glu

<210> SEQ ID NO 2
<211> LENGTH: 19
<212> TYPE: PRT
<213> ORGANISM: Influenza virus

<400> SEQUENCE: 2

```
Asn Val Pro Glu Lys Gln Thr Arg Gly Ile Phe Gly Ala Ile Ala Gly
1               5                   10                  15

Phe Ile Glu
```

<210> SEQ ID NO 3
<211> LENGTH: 19
<212> TYPE: PRT
<213> ORGANISM: Influenza virus

<400> SEQUENCE: 3

```
Pro Ala Lys Leu Leu Lys Glu Arg Gly Phe Phe Gly Ala Ile Ala Gly
1               5                   10                  15

Phe Leu Glu
```

<210> SEQ ID NO 4
<211> LENGTH: 30
<212> TYPE: PRT
<213> ORGANISM: Influenza virus

<400> SEQUENCE: 4

```
Gly Gly Ser Leu Leu Thr Glu Val Glu Thr Pro Ile Arg Asn Glu Trp
1               5                   10                  15

Gly Ser Arg Ser Asn Asp Ser Ser Asp Gly Gly Phe Glu Pro
            20                  25                  30
```

<210> SEQ ID NO 5
<211> LENGTH: 15
<212> TYPE: PRT
<213> ORGANISM: Influenza virus

<400> SEQUENCE: 5

```
Gly Met Ser Leu Leu Thr Glu Val Glu Thr Pro Ile Arg Gly Gly
1               5                   10                  15
```

<210> SEQ ID NO 6
<211> LENGTH: 16
<212> TYPE: PRT
<213> ORGANISM: Influenza virus

<400> SEQUENCE: 6

```
Gly Gly Met Ser Leu Leu Thr Glu Val Glu Thr Pro Ile Arg Gly Gly
1               5                   10                  15
```

<210> SEQ ID NO 7
<211> LENGTH: 20
<212> TYPE: PRT
<213> ORGANISM: Influenza virus

<400> SEQUENCE: 7

```
Met Asn Asn Ala Thr Phe Asn Tyr Thr Asn Val Asn Pro Ile Ser His
1               5                   10                  15

Ile Arg Gly Ser
            20
```

-continued

<210> SEQ ID NO 8
<211> LENGTH: 6
<212> TYPE: PRT
<213> ORGANISM: Influenza virus

<400> SEQUENCE: 8

```
Met Leu Glu Pro Phe Gln
1               5
```

<210> SEQ ID NO 9
<211> LENGTH: 24
<212> TYPE: PRT
<213> ORGANISM: Influenza virus

<400> SEQUENCE: 9

```
Met Ser Leu Leu Thr Glu Val Glu Thr Leu Thr Arg Asn Gly Trp Gly
1               5                   10                  15

Cys Arg Cys Ser Asp Ser Ser Asp
            20
```

<210> SEQ ID NO 10
<211> LENGTH: 42
<212> TYPE: DNA
<213> ORGANISM: Artificial
<220> FEATURE:
<223> OTHER INFORMATION: primer

<400> SEQUENCE: 10

```
gcatgccaca caccacttaa gtcagataag ctcacccagt tg                         42
```

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11

```
gcacggatgt gacagactga ag                                               22
```

<210> SEQ ID NO 12
<211> LENGTH: 40
<212> TYPE: DNA
<213> ORGANISM: Artificial
<220> FEATURE:
<223> OTHER INFORMATION: primer

<400> SEQUENCE: 12

```
cttaagtggt gtgtggcatg cctacggatg gagaaccgga                             40
```

<210> SEQ ID NO 13
<211> LENGTH: 29
<212> TYPE: DNA
<213> ORGANISM: Artificial
<220> FEATURE:
<223> OTHER INFORMATION: primer

<400> SEQUENCE: 13

```
agtggttttg tgtttgtcat ccaaaggtc                                        29
```

<210> SEQ ID NO 14
<211> LENGTH: 34
<212> TYPE: DNA
<213> ORGANISM: Artificial
<220> FEATURE:
<223> OTHER INFORMATION: primer

<400> SEQUENCE: 14
ggttggggtc ttaagtgcat ctagggcggc caat 34

<210> SEQ ID NO 15
<211> LENGTH: 43
<212> TYPE: DNA
<213> ORGANISM: Artificial
<220> FEATURE:
<223> OTHER INFORMATION: primer

<400> SEQUENCE: 15
acctcggtta gaaggctcat attatcatcg tgtttttcaa agg 43

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
atgagccttc taaccgaggt 20

<210> SEQ ID NO 17
<211> LENGTH: 35
<212> TYPE: DNA
<213> ORGANISM: Artificial
<220> FEATURE:
<223> OTHER INFORMATION: primer

<400> SEQUENCE: 17
ccaaccacag catgcttact ccagctctat gctga 35

<210> SEQ ID NO 18
<211> LENGTH: 8
<212> TYPE: PRT
<213> ORGANISM: Hepatitis C virus

<400> SEQUENCE: 18

Ser Thr Asn Pro Lys Pro Gln Arg
1 5

<210> SEQ ID NO 19
<211> LENGTH: 10
<212> TYPE: PRT
<213> ORGANISM: Hepatitis C virus

<400> SEQUENCE: 19

Tyr Leu Leu Pro Arg Arg Gly Pro Arg Leu
1 5 10

<210> SEQ ID NO 20
<211> LENGTH: 9
<212> TYPE: PRT
<213> ORGANISM: Hepatitis C virus

<400> SEQUENCE: 20

Gly Pro Arg Leu Gly Val Arg Ala Thr
1 5

<210> SEQ ID NO 21
<211> LENGTH: 20
<212> TYPE: PRT
<213> ORGANISM: Hepatitis C virus -continued

<400> SEQUENCE: 21

```
Tyr Pro Trp Pro Leu Tyr Gly Asn Glu Gly Cys Gly Trp Ala Gly Trp
1               5                   10                  15

Leu Leu Ser Pro
            20
```

<210> SEQ ID NO 22
<211> LENGTH: 16
<212> TYPE: PRT
<213> ORGANISM: Hepatitis C virus

<400> SEQUENCE: 22

```
Gly Phe Ala Asp Leu Met Gly Tyr Ile Pro Leu Val Gly Ala Pro Leu
1               5                   10                  15
```

<210> SEQ ID NO 23
<211> LENGTH: 9
<212> TYPE: PRT
<213> ORGANISM: Hepatitis C virus

<400> SEQUENCE: 23

```
Asp Leu Met Gly Tyr Ile Pro Leu Val
1               5
```

<210> SEQ ID NO 24
<211> LENGTH: 10
<212> TYPE: PRT
<213> ORGANISM: Hepatitis C virus

<400> SEQUENCE: 24

```
Leu Leu Ala Leu Leu Ser Cys Leu Thr Val
1               5                   10
```

<210> SEQ ID NO 25
<211> LENGTH: 20
<212> TYPE: PRT
<213> ORGANISM: Hepatitis C virus

<400> SEQUENCE: 25

```
Arg Glu Gly Asn Ala Ser Arg Cys Trp Val Ala Val Thr Pro Thr Val
1               5                   10                  15

Ala Thr Arg Asp
            20
```

<210> SEQ ID NO 26
<211> LENGTH: 9
<212> TYPE: PRT
<213> ORGANISM: Hepatitis C virus

<400> SEQUENCE: 26

```
Ser Thr Gly Leu Ile His Leu His Gln
1               5
```

<210> SEQ ID NO 27
<211> LENGTH: 10
<212> TYPE: PRT
<213> ORGANISM: Hepatitis C virus

<400> SEQUENCE: 27

```
Leu Leu Ala Asp Ala Arg Val Cys Ser Cys
1               5                   10
```

<210> SEQ ID NO 28
<211> LENGTH: 11
<212> TYPE: PRT
<213> ORGANISM: Hepatitis C virus

<400> SEQUENCE: 28

```
Cys Trp His Tyr Pro Pro Arg Pro Cys Gly Ile
1               5                   10
```

<210> SEQ ID NO 29
<211> LENGTH: 10
<212> TYPE: PRT
<213> ORGANISM: Hepatitis C virus

<400> SEQUENCE: 29

```
Cys Val Ile Gly Gly Val Gly Asn Asn Thr
1               5                   10
```

<210> SEQ ID NO 30
<211> LENGTH: 10
<212> TYPE: PRT
<213> ORGANISM: Hepatitis C virus

<400> SEQUENCE: 30

```
Arg Arg Leu Thr Asp Phe Ala Gln Gly Trp
1               5                   10
```

<210> SEQ ID NO 31
<211> LENGTH: 8
<212> TYPE: PRT
<213> ORGANISM: Hepatitis C virus

<400> SEQUENCE: 31

```
Thr Ile Asn Tyr Thr Ile Phe Lys
1               5
```

<210> SEQ ID NO 32
<211> LENGTH: 27
<212> TYPE: PRT
<213> ORGANISM: Hepatitis C virus

<400> SEQUENCE: 32

```
Glu Thr His Val Thr Gly Gly Asn Ala Gly Arg Thr Thr Ala Gly Leu
1               5                   10                  15

Val Gly Leu Leu Thr Pro Gly Ala Lys Gln Asn
            20                  25
```

<210> SEQ ID NO 33
<211> LENGTH: 27
<212> TYPE: PRT
<213> ORGANISM: Hepatitis C virus

<400> SEQUENCE: 33

```
Ile Gln Leu Ile Asn Thr Asn Gly Ser Trp His Ile Asn Ser Thr Ala
1               5                   10                  15

Leu Asn Cys Asn Glu Ser Leu Asn Thr Gly Trp
            20                  25
```

<210> SEQ ID NO 34
<211> LENGTH: 20
<212> TYPE: PRT
<213> ORGANISM: Hepatitis C virus

<400> SEQUENCE: 34

-continued

```
Leu Phe Tyr Gln His Lys Phe Asn Ser Ser Gly Cys Pro Glu Arg Leu
1               5                   10                  15

Ala Ser Cys Arg
            20


<210> SEQ ID NO 35
<211> LENGTH: 36
<212> TYPE: PRT
<213> ORGANISM: Hepatitis C virus

<400> SEQUENCE: 35

Pro Ser Pro Val Val Val Gly Thr Thr Asp Arg Ser Gly Ala Pro Thr
1               5                   10                  15

Tyr Ser Trp Gly Ala Asn Asp Thr Asp Val Phe Val Leu Asn Asn Thr
            20                  25                  30

Arg Pro Pro Leu
        35


<210> SEQ ID NO 36
<211> LENGTH: 6
<212> TYPE: PRT
<213> ORGANISM: Hepatitis C virus

<400> SEQUENCE: 36

Ile Gln Leu Ile Asn Thr
1               5


<210> SEQ ID NO 37
<211> LENGTH: 7
<212> TYPE: PRT
<213> ORGANISM: Human papilloma virus-16

<400> SEQUENCE: 37

Asp Arg Ala His Tyr Asn Ile
1               5


<210> SEQ ID NO 38
<211> LENGTH: 9
<212> TYPE: PRT
<213> ORGANISM: Human papilloma virus-16

<400> SEQUENCE: 38

Arg Ala His Tyr Asn Ile Val Thr Phe
1               5


<210> SEQ ID NO 39
<211> LENGTH: 5
<212> TYPE: PRT
<213> ORGANISM: Human papilloma virus-16

<400> SEQUENCE: 39

Glu Tyr Met Leu Asp
1               5


<210> SEQ ID NO 40
<211> LENGTH: 4
<212> TYPE: PRT
<213> ORGANISM: Human papilloma virus-16

<400> SEQUENCE: 40

Ile Asp Gly Pro
1
```

-continued

<210> SEQ ID NO 41
<211> LENGTH: 5
<212> TYPE: PRT
<213> ORGANISM: Human papilloma virus-16

<400> SEQUENCE: 41

Gln Ala Glu Pro Asp
1 5

<210> SEQ ID NO 42
<211> LENGTH: 11
<212> TYPE: PRT
<213> ORGANISM: Human papilloma virus-18

<400> SEQUENCE: 42

Val Asn His Gln His Leu Pro Ala Arg Arg Ala
1 5 10

<210> SEQ ID NO 43
<211> LENGTH: 10
<212> TYPE: PRT
<213> ORGANISM: Human papilloma virus-18

<400> SEQUENCE: 43

Asp Asp Leu Arg Ala Phe Gln Gln Leu Phe
1 5 10

<210> SEQ ID NO 44
<211> LENGTH: 336
<212> TYPE: DNA
<213> ORGANISM: Artificial
<220> FEATURE:
<223> OTHER INFORMATION: Synthetic

<400> SEQUENCE: 44
gagaaataca ctgactacct aacagtcatg gacaggtatt ctgtggatgc tgacctgcaa 60
ctgggtgagc ttatctgaaa caccatctaa caggaataac cgggatacaa accacgggtg 120
gagaaccgga ctccccacaa cctgaaaccg ggatataaac cacggctgga gaaccgggct 180
ccgcacttaa aatgaaacag aaaccgggat aaaaactacg gatggagaac cggactccac 240
acattgagac agaagaagtt gtcagcccag aaccccacac gagttttgcc actgctaagc 300
tgtgaggcag tgcaggctgg gacagccgac ctccag 336

<210> SEQ ID NO 45
<211> LENGTH: 23
<212> TYPE: PRT
<213> ORGANISM: Influenza virus

<400> SEQUENCE: 45

Ser Leu Leu Thr Glu Val Glu Thr Pro Ile Arg Asn Glu Trp Gly Cys
1 5 10 15

Arg Cys Asn Asp Ser Ser Asp
20

<210> SEQ ID NO 46
<211> LENGTH: 23
<212> TYPE: PRT
<213> ORGANISM: Influenza virus

<400> SEQUENCE: 46

Ser Leu Leu Thr Glu Val Glu Thr Pro Ile Arg Asn Glu Trp Gly Cys
1 5 10 15

-continued

```
Arg Cys Asn Gly Ser Ser Asp
            20


<210> SEQ ID NO 47
<211> LENGTH: 23
<212> TYPE: PRT
<213> ORGANISM: Influenza virus

<400> SEQUENCE: 47

Ser Leu Leu Thr Glu Val Glu Thr Pro Thr Lys Asn Glu Trp Gly Cys
1               5                   10                  15

Arg Cys Asn Asp Ser Ser Asp
            20


<210> SEQ ID NO 48
<211> LENGTH: 23
<212> TYPE: PRT
<213> ORGANISM: Influenza virus

<400> SEQUENCE: 48

Ser Leu Leu Thr Glu Val Glu Thr Pro Ile Arg Asn Glu Trp Glu Cys
1               5                   10                  15

Arg Cys Asn Gly Ser Ser Asp
            20


<210> SEQ ID NO 49
<211> LENGTH: 23
<212> TYPE: PRT
<213> ORGANISM: Influenza virus

<400> SEQUENCE: 49

Ser Leu Leu Thr Glu Val Glu Thr Pro Ile Arg Asn Glu Trp Glu Cys
1               5                   10                  15

Arg Cys Asn Asp Ser Ser Asp
            20
```